United States Patent [19]

Maine

[11] Patent Number: 4,936,529
[45] Date of Patent: Jun. 26, 1990

[54] DEVICE FOR DETECTING DEFECTIVE WHEELS ON RAIL CARS

[75] Inventor: Darren P. L. Maine, Calgary, Canada

[73] Assignee: Railbase Technologies, Incorporated, Alberta, Canada

[21] Appl. No.: 291,620

[22] Filed: Dec. 29, 1988

[51] Int. Cl.⁵ .................... B61K 3/00; E01C 23/00; G01R 27/04
[52] U.S. Cl. .................... 246/169 R; 73/146; 324/642
[58] Field of Search .......... 246/167 D, 169 R, 169 A, 246/169 D, 122 R, 247; 73/116, 146, 601, 618, 620; 324/58.5 A, 58.5 C, 58.5 B, 58 A

[56] References Cited

U.S. PATENT DOCUMENTS

| | | | |
|---|---|---|---|
| 2,301,251 | 11/1942 | Capen | 324/58.5 A X |
| 2,442,491 | 6/1948 | Gieskieng et al. | 246/169 R |
| 3,514,703 | 5/1970 | Soga | 324/58.5 C |
| 3,549,986 | 12/1970 | Prine | 324/58.5 A |
| 3,586,971 | 6/1971 | Bosisio | 324/58.5 C |
| 3,940,765 | 2/1976 | Grafinger et al. | 246/122 R |
| 4,076,192 | 2/1978 | Hoge | 246/247 |
| 4,700,127 | 10/1987 | Sasaki et al. | 73/116 X |

FOREIGN PATENT DOCUMENTS

| | | | |
|---|---|---|---|
| 3223126 | 12/1983 | Fed. Rep. of Germany | 246/247 |
| 1594032 | 6/1970 | France. | |
| 0033755 | 3/1977 | Japan | 324/58.5 C |
| 1183874 | 10/1985 | U.S.S.R. . | |
| 1193462 | 11/1985 | U.S.S.R. . | |
| 1200275 | 7/1970 | United Kingdom . | |
| 1326986 | 8/1973 | United Kingdom | 246/169 R |

OTHER PUBLICATIONS

"Microwaves", by Dr. K. C. Gupta, Wiley International, 1979.
"Association of American Railroads Wheel and Axle Manual", 3/1984.

*Primary Examiner*—Andres Kashnikow
*Assistant Examiner*—Timothy Newholm
*Attorney, Agent, or Firm*—Beveridge, DeGrandi & Weilacher

[57] ABSTRACT

Flanged steel wheels remain in service on rail cars, locomotives, and other heavy rail guided machinery unitl they no longer maintain minimum specified rim or flange profile dimensions. If the rim or flange profile of the wheel cannot be returned to minimum specifications by surface machining operations, the wheel is condemned as being defective and is removed from service and scrapped. It is desirable to use an automated inspection device to determine if a wheel is approaching this condemning limit of profile wear. The invention automatically detects profile defects upon passing the wheel between rail mounted antennae which form a resonator cavity and transmit microwave radiation. When influenced by a wheel possessing condemnable rim thickness, flange thickness, or flange height profiles, the antennae cause a D.C. voltage to propagate at a microwave detector inserted into an interconnected comparison bridge network. A controller monitors the detector and activates an alarm at a remote location when a voltage is detected. The alarm notifies operating personnel of a defective wheel and sequentially logs the date and time of the alarm occurrence, the axle and wheel position of the defective wheel, and the specific profile defect on the wheel.

16 Claims, 3 Drawing Sheets

Alloy Steel

High Carbon Steel

DEVICE FOR DETECTING DEFECTIVE WHEELS ON RAIL CARS

FIELD OF THE INVENTION

The invention pertains to a device for detecting defective wheels on rail cars. More particularly, the invention pertains to a device for automatically detecting high flange, thin rim, and thin flange surface profile defects on steel wheels of rail cars by utilizing microwave frequency resonator cavity networks.

BACKGROUND OF THE INVENTION

Prior to the invention, a manual gauging operation was performed in order to detect surface profile defects such as thin rim, high flange and thin flange profiles on the steel wheels of rail cars. This manual gauging was done using hand instruments and templates in accordance with standards and procedures set forth in the Association of American Railroads Wheel and Axle Manual (Section G, Part II) as well as the Field Interchange Manual. However, manual wheel gauging was extremely slow, labor intensive, and highly subjective. Furthermore, it could not be performed while the wheel was in motion.

Attempts at automating wheel inspection in the railroad industry include a high flange detection device disclosed in U.S. Pat. No. 4,076,192, and a wheel flange inspection device marketed by Wheel Checkers Ltd. of Denver, Colorado, USA, under the trade name WHEEL CHECKER. These devices mechanically detect a flange profile defect by relying on a defective flange to contact a gauging surface which actuates an alarm when contact is made. However, these devices have proven unsatisfactory due to their mechanical nature, their inability to detect profile defects other than on the flange of the wheel, and their difficulty in upgrading associated signal methods.

A further attempt at automating wheel inspection includes a wheel profiling system recently introduced by Hegenscheidt Corporation. This system utilizes laser optics to effect non-surface contact profiling of in-motion wheels. However, this system has been evaluated and determined to be an unsatisfactory approach for automated detection of wheel profile defects because it uses light sensitive optics which are unreliable in the dirty and rough service environments typical of North American heavy freight railroad operations. All-weather protection as well as ambient light exclusion would be essential for effective operation of this system. Accordingly, the construction of pull-through sheds of approximately two to three car lengths in size would be necessary to accommodate the system. Further disadvantages include difficulty in using the system at locations isolated from terminal points, inability to group individual profiler installations into multi-unit networks controlled by a centralized computer, and extremely high purchase costs associated with the system.

SUMMARY OF THE INVENTION

The invention utilizes a microwave resonator cavity and a comparison bridge network as means for performing flange and rim profiling of an in-motion wheel of a rail car. The microwave resonator cavity comprises a microwave frequency radiation transmission path existing between antennae. The antennae are oriented normal to and span the gauging point of the rim or flange of the wheel to be inspected. The invention inspects the wheel for profile defects without utilizing mechanical contacts. Furthermore, by utilizing microwave radiation rather than laser light, the invention eliminates the problems associated with optical methods of inspection.

The invention can form an inspection system which simultaneously detects rim thickness, flange height, and flange thickness defects by using several microwave resonator cavities. The invention can also be incorporated into an inspection system which includes modern hot box (wheel journal bearing temperature) detectors, and can be integrated into multiple unit networks monitored from a single centralized computer.

DETAILED DESCRIPTION OF A PREFERRED EMBODIMENT

Figure 1:
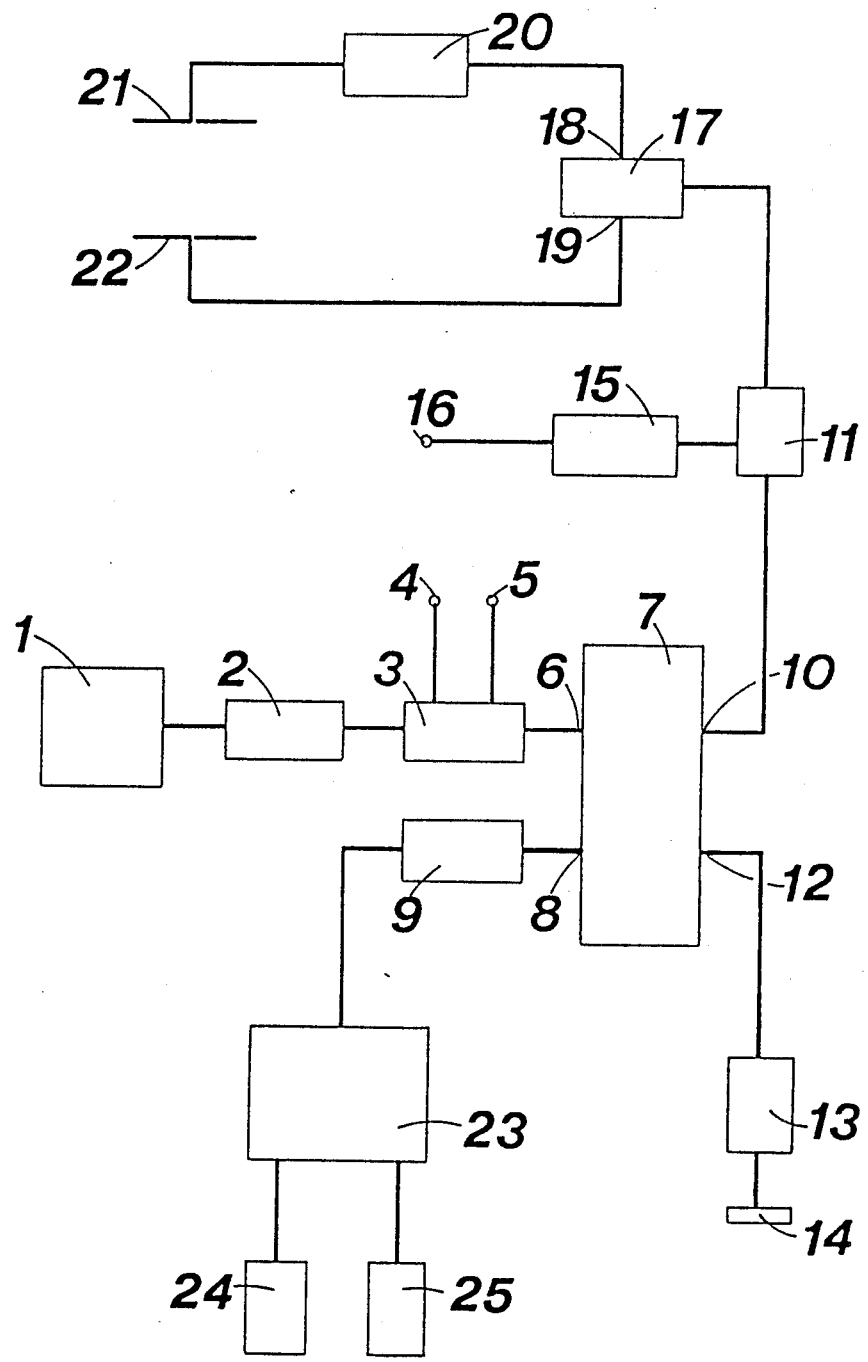
FIG. 1 shows a block diagram of a microwave frequency resonator cavity and comparison bridge assembly in accordance with a preferred embodiment of the invention.

FIG. 1 shows a comparison bridge portion and a resonator cavity portion of a microwave network that can detect high flange, thin rim, and thin flange surface profile defects on a steel wheel. The comparison bridge portion of the microwave network comprises a radio frequency microwave source 1, an attenuator 2, and a single pole, single throw (SPST) microwave switch 3 which is closed by introducing a first voltage to a first input 4 and is opened by applying a second voltage to a second input 5. The microwave signal feeds forward from the switch 3 to a summing port 6 of a four-port 0 degree/180 degree hybrid coupler 7. The other three ports of the hybrid coupler 7 include a difference port 8 coupled to a microwave detector 9, a 0 degree port 10 coupled to a directional coupler 11, and a 180 degree port 12 coupled to a tuner 13 which terminates at a microwave termination 14. The directional coupler 11 is, in turn, coupled to a second microwave detector 15 having an output 16 accessible for monitoring during network tuning.

The resonator cavity portion of the microwave network comprises a three-port circulator 17 having a phase shifter 20 and an antenna 21 connected to a port 18, and an antenna 22 connected to a port 19. A controller 23 monitors the output of the microwave detector 9 for development of a direct current (D.C.) voltage. The output of the controller 23 is connected to an alarm device 24 and an annunciator/printer 25. All the components of the network are interconnected using either microwave quality waveguide, coaxial cable, or stripline transmission lines equipped for interconnection with the network components.

The network is tuned by adjusting the tuner 13 and the phase shifter 20 until the voltage output, which represents the network standing wave ratio from the microwave detectors 9 and 15, is at a minimum value when the resonator cavity is influenced by a wheel having normal rim or flange profile dimensions. Sensitivity of the resonator cavity, i.e. the ability of the resonator cavity to detect dimensional variations of a small order on the flange or rim profiles, is adjustable by increasing or decreasing the frequency of the incidental microwave radiation generated by the microwave source 1.

The network of the invention is based on a network suggested by Dr. K. C. Gupta in "Microwaves", Wiley International, 1979. As disclosed by Dr. Gupta, microwaves are useful for measuring the thickness of metal sheets in rolling mills. At microwave frequencies, metals exhibit very small skin depths, and thus, microwaves are essentially totally reflected at the surface of a metal. Because wavelengths of microwaves are small and phase variations are rapid, a small discrepancy in thickness of the metal gives rise to a significant phase change that can be detected and measured. Variations of Dr. Gupta's basic network can also be found in foreign patents SU 1193462, SU 1183874 and FR 1594032, which relate to microwave frequency, resonator cavity-type gauging devices for metallic phase materials.

Figure 2:
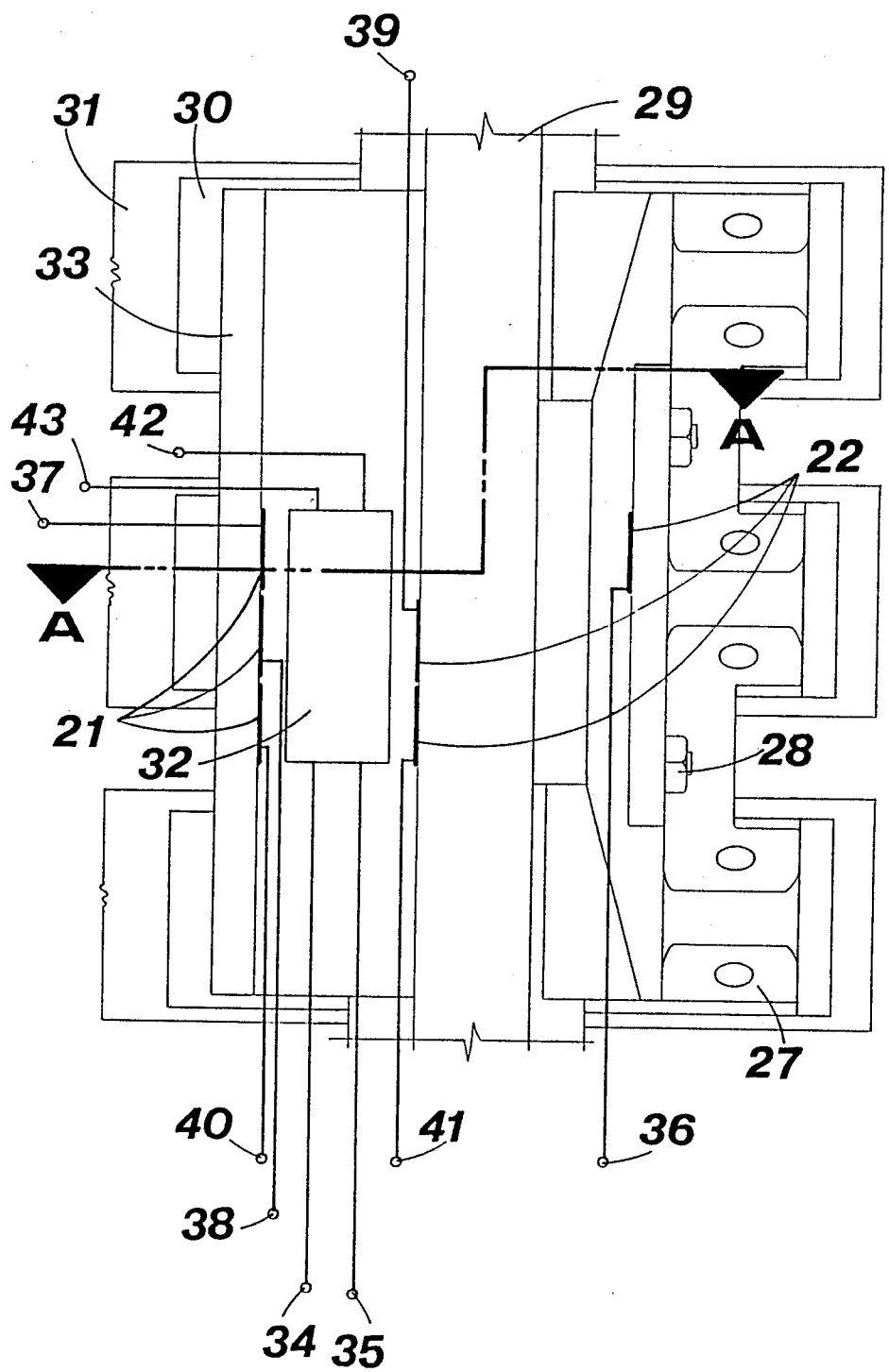
FIG. 2 shows a plan view of a three-point profile inspection system in accordance with a preferred embodiment of the invention.
Figure 3:
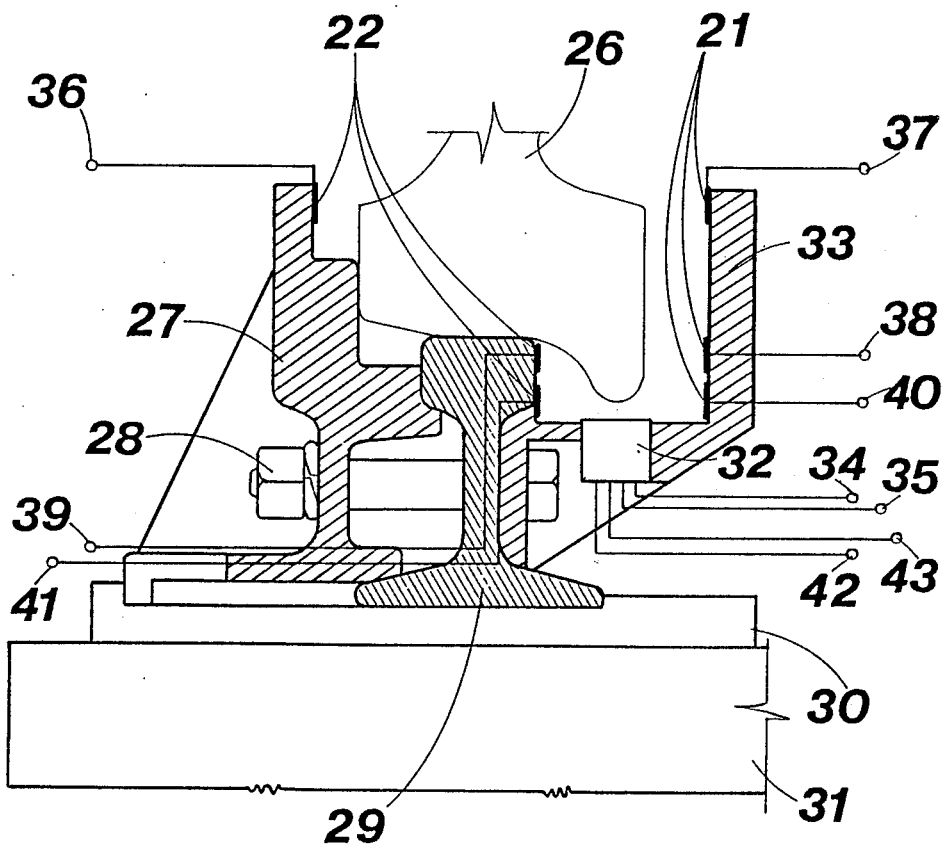
FIG. 3 shows a section view along line A—A of FIG. 2.
Figure 3:

FIGS. 2 and 3 show a system which utilizes the network described supra to detect high flange, thin rim, and thin flange surface profile defects on the rim and flange profile of a steel wheel on a rail car. The comparison bridge portion of the network is identical for either thin rim, thin flange, or high flange detection. Only the placement of the antennae 21 and 22 will vary for each unique gauging function.

Referring to FIG. 3, a wheel 26 to be inspected encounters a guard rail 27 positioned on one side of a running rail 29. A flangeway guard rail 33 is positioned on the other side of the running rail 29 opposite the guard rail 27. The guard rails 27 and 28 are connected to the running rail 29 by means of a bolt assembly 28. The entire rail assembly is rigidly mounted by means of gauge plate 30 to cross tie 31.

A magnetically actuated double pole, double throw (DPDT) proximity limit switch 32 is mounted into the flangeway guard rail 33 and is normally closed until influenced by the wheel 26. When the wheel 26 becomes proximate with the switch 32, the switch contacts will open to thereby feed a voltage from a power supply line 34 via a supply line 35 to the port 4 of the SPST microwave switch 3 shown in FIG. 1. This causes the contacts of the SPST microwave switch 3 to close, which in turn allows the microwave network to become energized.

The rim and flange of the wheel 26 influence the microwave radiation propagating between antennae 21 and 22 configured in three sets as thin rim, thin flange, and high flange detecting cavities. The antennae 21 and 22 are interconnected through lines 36 and 37 for thin rim detection, lines 38 and 39 for thin flange detection, and lines 40 and 41 for high flange detection. The sets of antennae 21 and 22 have respective individual networks including the port 18, the phase shifter 20 and the port 19 of the three port circulator 17 shown in FIG. 1.

The microwave detector 9 is continuously monitored by the controller 23. Should a voltage develop at detector 9 in any of the networks, the controller 23 quantifies the voltage to interpret the signal to flange height, flange thickness, and rim thickness values and compares the resulting values to preset alarm levels. If these preset levels are exceeded, the controller 23 will activate the visual and audible alarms 24, and the printer 25 will log the time and date of the alarm event, the axle count of the defective wheel as determined by a rail mounted axle counter, the position of the defective wheel relative to the left or right side of the axle, and whether a thin rim, a thin flange, a high flange or a combination of these defects was detected. The controller 23 is then externally reset to return it to a monitor mode. Once the wheel 26 is no longer proximate with the proximity limit switch 32, the switch contacts will open to thereby feed a second voltage from a power supply line 42 via a supply line 43 to the port 5 of the SPST microwave switch 3. This causes the contacts of the SPST microwave switch 3 to open, which in turn allows the microwave network to become de-energized.

The invention is effective for inspecting wheels of locomotives, railroad cars, and other heavy industrial rail-guided machinery such as cranes and mining equipment. With no alterations, the invention can also be adapted for inspecting wheels of light-rail transit cars. It may be used for inspecting new or in-service wheels, irrespective of whether the wheels are axle or equipment mounted. The invention can also be adapted to fit any track gauge or rail type.

Although the invention has been described with reference to a preferred embodiment, numerous modifications and rearrangements can be made with the result still coming within the scope of the invention.

What is claimed is:

1. A device for detecting surface profile defects on a metal wheel having a rim and a flange and adapted to run along a railway, comprising:
    a resonator cavity, mounted proximate said railway, for causing reflection of microwave energy from the surface of said wheel; and
    a microwave detector, connected to said resonator cavity, for measuring said reflection and determining surface profile defects in said wheel.

2. A device according to claim 1 wherein said resonator cavity comprises microwave frequency antennae positioned to gauge said wheel.

3. A device according to claim 2 wherein said microwave frequency antennae are positioned at both sides of said wheel.

4. A device according to claim 2 wherein said microwave frequency antennae are mounted normal to a gauging point of said wheel.

5. A device according to claim 1 further comprising:
    a controller, connected to said detector, for monitoring output of said microwave detector and causing an alarm event to indicate a defect in said wheel.

6. A device according to claim 1, wherein a plurality of resonators are provided to form a profiling station for detecting surface profile defects in said rim and said flange of said wheel.

7. A device according to claim 6 wherein said resonators comprises microwave frequency antennae positioned to gauge said rim and said flange of said wheel.

8. A device for detecting thin flange, high flange, and thin rim-type surface profile defects on in-motion flanged steel heels, comprising:
    a running-rail and guard-rail assembly having pairs of intermittently-energized microwave antennae arranged so that the rim and flange of said wheel pass between individual antennae of said pairs of antennae without surface contact;
    microwave bridges interconnected with said pairs of antennae so that one set of paired antennae and its associated microwave bridge comprises a thin flange-type defect detector, one set comprises a high flange-type defect detector, and one set comprises a thin rim-type defect detector; and
    a controller individually-monitoring outputs from said high flange detector, said thin flange detector, and said thin rim detector, and activating an alarm should a thin flange, high flange, or thin rim-type surface profile defect be detected on the rim or flange of said wheel.

9. A detecting device according to claim 8, further comprising:
   a proximity-actuated limit switch controlling intermittent energizing of said this flange detector, said high flange detector, and said thin rim detector while said wheel is proximate an appropriate detector set.

10. A detecting device according to claim 9 wherein said switch is mounted on said guard-rail and is closed until influenced by said wheel.

11. A detecting device according to claim 10 wherein said wheel influences said switch to open when said wheel is proximate said switch, thereby energizing said detectors.

12. A detecting device according to claim 8, further comprising:
   a microwave source energizing said detectors while the flange and rim of said wheel are proximate said thin flange detector, said high flange detector, and said thin flange detector in sequence.

13. A detecting device according to claim 8, wherein said controller compares said outputs generated from said detector to preset output limits directly proportional to predetermined flange and rim surface profile dimensions, and activates an alarm signal if any of said outputs corresponds with said output limits indicating a thin flange, high flange, or thin rim-type surface profile on said wheel.

14. A detecting device according to claim 8 wherein three pairs of antennae are arranged on said assembly.

15. A detecting device according to claim 8 wherein said running-rail and guard-rail assembly includes a running-rail and a guard-rail positioned along each aide of said running-rail.

16. A detecting device according to claim 15 wherein said antennae are mounted on said guard-rail and said running-rail.

* * * * *